United States Patent
Witte et al.

(10) Patent No.: US 9,915,667 B2
(45) Date of Patent: Mar. 13, 2018

(54) METHODS AND MEANS FOR DIAGNOSING VASCULITIS

(75) Inventors: Torsten Witte, Hannover (DE); Niklas Thomas Baerlecken, Hannover (DE)

(73) Assignee: MEDIZINISCHE HOCHSCHULE HANNOVER, Hannover (DE)

( * ) Notice: Subject to any disclaimer, the term of this patent is extended or adjusted under 35 U.S.C. 154(b) by 0 days.

(21) Appl. No.: 13/981,956

(22) PCT Filed: Jan. 27, 2012

(86) PCT No.: PCT/EP2012/051301
§ 371 (c)(1),
(2), (4) Date: Jul. 26, 2013

(87) PCT Pub. No.: WO2012/101246
PCT Pub. Date: Aug. 2, 2012

(65) Prior Publication Data
US 2013/0310273 A1    Nov. 21, 2013

(30) Foreign Application Priority Data

Jan. 27, 2011    (EP) .................................... 11152361

(51) Int. Cl.
*G01N 33/564* (2006.01)
*G01N 33/68* (2006.01)
(Continued)

(52) U.S. Cl.
CPC ..... *G01N 33/6893* (2013.01); *A61K 39/0008* (2013.01); *G01N 33/564* (2013.01);
(Continued)

(58) Field of Classification Search
None
See application file for complete search history.

(56) References Cited

U.S. PATENT DOCUMENTS

| 7,799,900 B2 * | 9/2010 | Adams ............... C07K 16/2887 |
| | | 530/350 |
| 2003/0175884 A1 * | 9/2003 | Umana ............... C12N 9/1051 |
| | | 435/69.1 |
| 2004/0101909 A1 * | 5/2004 | Lemieux et al. ............. 435/7.1 |

FOREIGN PATENT DOCUMENTS

EP    1 394 183    3/2004

OTHER PUBLICATIONS

Wood (1981) "A Comparison of Eleven Commercial Kits for the Determination of Serum Ferritin Levels" J. Clin. Chem. Clin. Biochem. 19:947-952.*

(Continued)

*Primary Examiner* — Karen S. Weiler
(74) *Attorney, Agent, or Firm* — Whitham, Curtis & Cook, P.C.

(57) ABSTRACT

Provided herein are methods for diagnosing the presence or the risk of development, or for the therapy control of vasculitis, in particular of large vessel vasculitis, like giant-cell arteritis (GCA), polymyalgia rheumatica (PMR), and Takayasu's arteritis, in a subject analyzing for the presence of antibodies against ferritin, in particular heavy chain ferritin or immunoreactive peptides thereof or ferritin analog protein, preferably bacterial ferritin analog protein, or immunoreactive peptides thereof, in a subject. In addition, test kits for use in the diagnosis of the presence or the risk of development, or for the therapy control of vasculitis, in particular of large vessel vasculitis, like GCA, PMR and Takayasu's arteritis, in a subject are also provided.

14 Claims, 4 Drawing Sheets

(51) Int. Cl.
 *A61K 39/00* (2006.01)
 *C07K 16/44* (2006.01)
(52) U.S. Cl.
 CPC ........ *C07K 16/44* (2013.01); *G01N 2800/101* (2013.01); *G01N 2800/328* (2013.01); *G01N 2800/50* (2013.01); *G01N 2800/52* (2013.01)

(56) References Cited

OTHER PUBLICATIONS

Tort, Suzy V., et al., "Human H-kininogen is a Ferritin-binding Protein", J. of Biological Chemistry, vol. 273, No. 22, (May 1998) pp. 13630-13635.
Castro, C., et al., "Diagnostic Testing and Interpretation of Tests for Autoimmunity", J. of Allergy and Clinical Immunology, vol. 125, No. 2 (Feb. 2010) pp. S238-S247.
Williams, M.J.A., et al., "Relationship of Serum Ferritin with Cariovascular Risk Factors and Inflammation in Young Men and Women", Atherosclerosis, vol. 165, No. 1, (Nov. 2002), pp. 179-184.
Cunha, B.A., "Fever of Unknown Origin Caused by Adult Juvenile Rheumatoid Arthritis: the Diagnostic Significance of Double Quotidian Fevers and Elevated Serum Ferritin levels", Heart and Lung, vol. 33, No. 6, (Nov. 2004) pp. 417-421.
Zenone, T., "Fever of Unknown Origin in Rheumatic Diseases", Infectious Disease Clinics of North America, vol. 21, No. 4 (Dec. 2007) pp. 1115-1135.

* cited by examiner

```
                         SEQUENCE LISTING

<160> NUMBER OF SEQ ID NOS: 6

<210> SEQ ID NO 1
<211> LENGTH: 183
<212> TYPE: PRT
<213> ORGANISM: human

<400> SEQUENCE: 1

Met Thr Thr Ala Ser Thr Ser Gln Val Arg Gln Asn Tyr His Gln Asp
1               5                   10                  15

Ser Glu Ala Ala Ile Asn Arg Gln Ile Asn Leu Glu Leu Tyr Ala Ser
                20                  25                  30

Tyr Val Tyr Leu Ser Met Ser Tyr Tyr Phe Asp Arg Asp Asp Val Ala
            35                  40                  45

Leu Lys Asn Phe Ala Lys Tyr Phe Leu His Gln Ser His Glu Glu Arg
    50                  55                  60

Glu His Ala Glu Lys Leu Met Lys Leu Gln Asn Gln Arg Gly Gly Arg
65                  70                  75                  80

Ile Phe Leu Gln Asp Ile Lys Lys Pro Asp Cys Asp Asp Trp Glu Ser
                85                  90                  95

Gly Leu Asn Ala Met Glu Cys Ala Leu His Leu Glu Lys Asn Val Asn
            100                 105                 110

Gln Ser Leu Leu Glu Leu His Lys Leu Ala Thr Asp Lys Asn Asp Pro
        115                 120                 125

His Leu Cys Asp Phe Ile Glu Thr His Tyr Leu Asn Glu Gln Val Lys
    130                 135                 140

Ala Ile Lys Glu Leu Gly Asp His Val Thr Asn Leu Arg Lys Met Gly
145                 150                 155                 160

Ala Pro Glu Ser Gly Leu Ala Glu Tyr Leu Phe Asp Lys His Thr Leu
                165                 170                 175

Gly Asp Ser Asp Asn Glu Ser
            180

<210> SEQ ID NO 2
<211> LENGTH: 166
<212> TYPE: PRT
<213> ORGANISM: staphylococcus

<400> SEQUENCE: 2

Met Leu Ser Lys Glu Leu Leu Ala Ala Leu Asn Glu Gln Met Asn Gln
1               5                   10                  15

Glu Tyr Phe Ala Ala His Ala Tyr Met Ala Met Ala Ala Tyr Cys Asp
                20                  25                  30

Lys Glu Ser Tyr Asp Gly Phe Ala Asn Phe Tyr Ile Glu Gln Ala Lys
            35                  40                  45

Glu Glu Arg Phe His Gly Lys Lys Ile Tyr Asp Tyr Ile Asn Asp Arg
    50                  55                  60

Gly Glu His Ala Ile Phe Asp Thr Ile Lys Ala Pro Lys Val Glu Phe
65                  70                  75                  80

Ser Ser Ile Leu Glu Thr Phe Lys Asp Ser Leu Ala Gln Glu Arg Asp
                85                  90                  95
```

```
Val Thr Gln Arg Phe Tyr Asn Leu Ser Glu Leu Ala Arg Asn Asp Lys
            100                 105                 110

Asp Tyr Ala Thr Ile Ser Phe Leu Asn Trp Phe Leu Asp Glu Gln Val
        115                 120                 125

Glu Glu Glu Ser Thr Phe Glu Thr His Ile Asp Tyr Leu Thr Arg Ile
    130                 135                 140

Gly Asp Asp Cys Asn Thr Leu Tyr Leu Tyr Gly Lys Glu Leu Ala Ala
145                 150                 155                 160

Arg Ser Phe Asn Glu Gln
                165

<210> SEQ ID NO 3
<211> LENGTH: 27
<212> TYPE: PRT
<213> ORGANISM: human

<400> SEQUENCE: 3

Ala Ala Ile Asn Arg Gln Ile Asn Leu Glu Leu Tyr Ala Ser Tyr Val
1               5                   10                  15

Tyr Leu Ser Met Ser Tyr Tyr Phe Asp Arg Asp
            20                  25

<210> SEQ ID NO 4
<211> LENGTH: 27
<212> TYPE: PRT
<213> ORGANISM: staphylococcus

<400> SEQUENCE: 4

Ala Ala Leu Asn Glu Gln Met Asn Gln Glu Tyr Phe Ala Ala His Ala
1               5                   10                  15

Tyr Met Ala Met Ala Ala Tyr Cys Asp Lys Glu
            20                  25

<210> SEQ ID NO 5
<211> LENGTH: 26
<212> TYPE: PRT
<213> ORGANISM: human

<400> SEQUENCE: 5

Gly Arg Ile Phe Leu Gln Asp Ile Lys Lys Pro Asp Cys Asp Asp Trp
1               5                   10                  15

Glu Ser Gly Leu Asn Ala Met Glu Cys Ala
            20                  25

<210> SEQ ID NO 6
<211> LENGTH: 40
<212> TYPE: PRT
<213> ORGANISM: human

<400> SEQUENCE: 6

Leu His Leu Glu Lys Asn Val Asn Gln Ser Leu Leu Glu Leu His Lys
1               5                   10                  15

Leu Ala Thr Asp Lys Asn Asp Pro His Leu Cys Asp Phe Ile Glu Thr
            20                  25                  30

His Tyr Leu Asn Glu Gln Val Lys
            35                  40
```

METHODS AND MEANS FOR DIAGNOSING VASCULITIS

FIELD OF THE INVENTION

The present invention relates generally to methods for diagnosing the presence or the risk of development or the therapy control of vasculitis, in particular of large vessel vasculitis, like giant-cell arteritis (GCA), polymyalgia rheumatica (PMR) and Takayasu's arteritis in a subject, in particular, in mammals. In addition, the present invention relates to test kits for use in the diagnosis of the presence or the risk of development, or for the therapy control of vasculitis, in particular of large vessel vasculitis, like GCA, PMR and Takayasu's arteritis, in a subject. In particular, the present invention relates to a method for diagnosing the presence or the risk of development, or for the therapy control of vasculitis, in particular of large vessel vasculitis, like GCA, PMR and Takayasu's arteritis, in a subject analyzing for the presence of antibodies against ferritin, in particular, heavy chain ferritin, or immunoreactive peptides thereof or ferritin analog protein, preferably bacterial ferritin analog protein, or immune-reactive peptides thereof, in a subject. The presence of antibodies against ferritin or immunoreactive peptides thereof is indicative for the presence or the risk of development, or for the therapy control of vasculitis, in particular of large vessel vasculitis, like GCA, PMR and Takayasu's arteritis. That is, detection of the presence of antibodies against ferritin or immunoreactive peptides thereof, allows early diagnosis of vasculitis, in particular of large vessel vasculitis, like GCA, PMR and Takayasu's arteritis.

BACKGROUND OF THE INVENTION

Vasculitis refers to a heterogeneous group of disorders leading to inflammatory destruction of blood vessels. Both, arteries and veins may be affected. Classification of vasculitis can take place by indicating the underlying cause, the location of the affected vessels or the type or size of the blood vessels predominantly attacked. Usually, there is an immune component, but the triggering incident is often unknown. In cases autoantibodies are found said autoantibodies are sometimes used for disease classification, as in ANCA (anti neutrophil cytoplasmic antibody)-associated vasculitides. ANCAs are found in patients with small vessel vasculitides, like Wegener's granulomatosis (WG), Microscopic polyangitis (MPA) and Churg Strauss syndrome (CSS). However, cANCA have been found only in 40% and pANCA only in 50% of MPA-patients. In CSS-patients, cANCA as well as pANCA were detectable only in 35 of 100 patients. Hence, the provision of diagnostic markers, particularly for early diagnosis, as well as for the identification of the status of disease and for the stratification of therapy regimen is still a challenge in vasculitis. This is particularly true with large vessel vasculitis, as detailed below.

An overview on polymyalgia rheumatica and giant-cell disease has been given by Salvarani, C. et al., Lancet 2008, 372: 234-245. Giant-cell arteritis (GCA) (also known as Morbus Horton or *Arteriitis cranialis*) is the main primary systemic vasculitis with a prevalence of 1:500 to 1:1000 in over 50 years old persons in Germany, affecting three times more women than men. GCA affects large and medium-sized vessels whereby inflammation occur mainly in the branches of the *A. carotis* externa. Intracranial vessels are seldom involved. Thirty to sixty percent of patients with GCA are concomitantly affected with polymyalgia rheumatica (PMR). Both, aetiology and pathogenesis of GCA are presently unknown. Viral infections (with Parainfluenza virus type 1 or Parvovirus B19) and infection with *Mycoplasma pneumoniae* have been discussed as triggering events for manifestation of GCA.

Histological findings include granulomatous panarteritis of medium- and large-sized arteries with giant-cells (of Langerhans and of foreign body type), infiltration of lymphomononuclear cells (mainly of $CD4_+$ T-cells and macrophages) and stenosed vessel lumen due to proliferation of the intima. Since clonal T-cell expansion is a frequent finding, reaction to a specific antigen is likely.

A cardinal symptom of GCA is headache, occurring mainly unilaterally and localized frontotemporally. The most severe complication occurring in up to ⅓ of patients is blindness due to inflammation of ciliar arteries leading to anterior ischaemic opticus neuropathy. Since this kind of damage to the opticus nerve is nearly irreversible, immediate onset of therapy with cortisone is mandatory when GCA is suspected.

In 10 to 20 percent of patients with GCA only large vessels are affected instead of the temporal arteries and blindness is unlikely. However, thoracic aortitis is often causative of aortic aneurysms and dissections.

Often association of GCA with PMR is found, leading to symmetric myalgia in shoulder, pelvic and neck musculature. Diagnosis of PMR is done by combining clinical symptoms, excluding other diseases and by monitoring the response to glucocorticoids. Pathological findings are much less prominent than in GCA and include a mild synovitis characterized by a predominance of macrophages and $CD4_+$ T-lymphocytes in synovial membranes of involved joints. Until now, analyzing a biopsy of the temporal arteries remains the gold standard in diagnosing GCA, despite two studies drawn up showing a sensitivity up to 90% in diagnosing GCA with high resolution color duplex sonography (used to demonstrate possible vascular wall edema) and with gadolinium-based high-resolution 1.5 or 3 Tesla magnet resonance tomography.

Takayasu's arteritis also known as "aortic arch syndrome" is related to GCA. It is characterized by large vessel granulomatous vasculitis with massive intimal fibrosis and stenosed vessel lumen due to massive intimal fibrosis.

Since complete remission is achievable in case of early diagnosis, there is need for diagnostic markers of vasculitis, in particular, of markers allowing early diagnosis of said diseases, especially for large vessel vasculitis, like GCA, PMR and Takayasu's arteritis.

Up to now no specific diagnostic marker has been established although genetic association of GCA with HLA-DRB1*04 alleles have been described. In patients with PMR the strength of association with HLA-DRB1 varies between different populations. Subjects with variations in HLA-DR*04 alleles are at higher risk of developing GCA and PMR, but analyzing the HLA-DRB1*04 alleles is not suited as a diagnostic test in an individual (Dejaco, C. et al., Akt Rheumatol, 2009, 34, 180-184).

Autoantibodies associated with rheumatoid arthritis (RA) are known (WO 2010/075249). Moreover, autoantibodies against ferritin heavy chain have been detected in patients with rheumatoid arthritis indicating the severity of joint damage (Mewar, D. et al., Arthritis and Rheumatism, Vol. 52, No. 12, 2005, 3868-3872).

In view of the above, there is an ongoing need for providing a diagnostic tool and method allowing diagnosis and assessing the risk of developing vasculitis, in particular, large vessel vasculitis, like GCA, PMR and Takayasu's arteritis, as well as for providing a tool and method for therapy control of vasculitis, in particular large vessel vasculitis, like GCA, PMR and Takayasu's arteritis.

BRIEF DESCRIPTION OF THE PRESENT INVENTION

The present invention provides a diagnostic method for the presence or the risk of developing vasculitis, in particular, large vessel vasculitis, like giant-cell arteritis (GCA), polymyalgia rheumatica (PMR) and Takayasu's arteritis, as well as for therapy control of vasculitis, like GCA, PMR and Takayasu's arteritis, in a subject. That is, the present inventors recognized that subjects suffering from vasculitis, particularly from large vessel vasculitis, like GCA, PMR and Takayasu's arteritis, have antibodies directed against ferritin, in particular, against the heavy chain of ferritin, or immunoreactive peptides thereof, preferably human ferritin or bacterial ferritin, or immunoreactive peptides thereof. Hence, early diagnosis of vasculitis, in particular of large vessel vasculitis, like giant-cell arteritis, polymyalgia rheumatica and Takayasu's arteritis, is possible before invasive and/or cost-intensive procedures have to be performed.

Thus, a first embodiment of the present invention relates to a method for diagnosing the presence or the risk of development, or for the therapy control of vasculitis, in particular of large vessel vasculitis, like GCA, PMR and Takayasu's arteritis, in a subject comprising
  a. providing a biological sample from a subject to be tested, for example, obtaining a biological sample from the subject, and
  b. analyzing the sample for the presence of antibodies against ferritin, in particular, heavy chain ferritin, or immunoreactive peptides thereof,
whereby the presence of antibodies against ferritin, in particular, heavy chain ferritin, or immunoreactive peptides thereof, is indicative of the presence or the risk of development, or for the therapy control of vasculitis, in particular of large vessel vasculitis, like GCA, PMR and Takayasu's arteritis.

Preferably, the biological sample is one from a human subject. Typically, the presence of antibodies against human ferritin, i.e. autoantibodies, or against a non-human ferritin protein, preferably, antibodies against human ferritin heavy chain and/or bacterial ferritin, or immunoreactive peptides thereof, are detected.

Alternatively or in addition, it is preferred that antibodies against bacterial ferritin or immune reactive peptides thereof, are detected.

Preferably said detection of antibodies is conducted using immunoassays, like ELISA. Typically, the biological sample to be tested is obtained from blood, in particular serum.

Thus, the diagnostic method according to the present invention represents the first method allowing positive diagnosis of vasculitis, e.g. large vessel vasculitis, like GCA, PMR and Takayasu's arteritis in a subject via antibody markers. Diagnosis is possible at an early stage of the disease as well as during therapy. Another embodiment of the present invention relates to a test kit for use in a method according to the present invention, namely for diagnosing the presence or the risk of a development as well as for therapy control of vasculitis, particularly of large vessel vasculitis, like GCA, PMR and Takayasu's arteritis, in a subject comprising means of determining antibodies against ferritin, particularly against ferritin heavy chain, and immunoreactive peptides thereof, in a biological sample of a subject to be tested and instruction on how to use said test kit. Preferably, the test kit is an ELISA assay.

BRIEF DESCRIPTION OF THE DRAWINGS

FIG. 1.

FIG. 2: The figure shows the titers of IgG-antibodies against the human ferritin heavy chain (Seq. ID. No. 1) in different diseases corresponding to the data shown in FIG. 1. The titer is considered positive, if it is 0.6 U/ml or higher (cut-off 0.6 U/ml). From the left to the right the different test groups are listed: GCA FD=giant cell arteritis (first diagnosis), PMR FD=polymyalgia rheumatica (first diagnosis), PMR GCA FD=polymyalgia rheumatica giant cell arteritis (first diagnosis), GCA=giant cell arteritis, PMR=polymyalgia rheumatica, PMR GCA=polymyalgia rheumatica giant cell arteritis, MPA=microscopic polyangiitis, active MPA=active microscopic polyangiitis, CSS active=Churg-Strauss-syndrome (active), WG=Wegener's granulomatosis, SLE=systemic lupus erythematosus, fever, HIV=human immune deficiency virus, and blood donors.

FIG. 3.

FIG. 4: The figure shows the percentage of positive patients for anti-ferritin bacterial protein, here the peptide of Seq. ID. No. 4, in different diseases: GCA/PMR=giant cell arteritis/polymyalgia rheumatica, GCA FD=giant cell arteritis (first diagnosis), treated GCA=treated giant cell arteritis, treated active GCA=treated active giant cell arteritis, PMR=polymyalgia rheumatica, PMR FD=polymyalgia rheumatica (first diagnosis), treated PMR=treated polymyalgia rheumatica, PMR and GCA combined=polymyalgia rheumatica and giant cell arteritis combined, PMR and GCA combined FD=polymyalgia rheumatica and GCA combined (first diagnosis), treated PMR and GCA combined=treated polymyelitis rheumatica and giant cell arteritis combined, active SLE=active systemic lupus erythematosus, active RA=active rheumatoid arthritis, MD=malignant diseases, HIV=human immune deficiency virus, fever, AS=ankylosing spondylitis, and blood donors.

DETAILED DESCRIPTION OF THE PRESENT INVENTION

Figure 1:
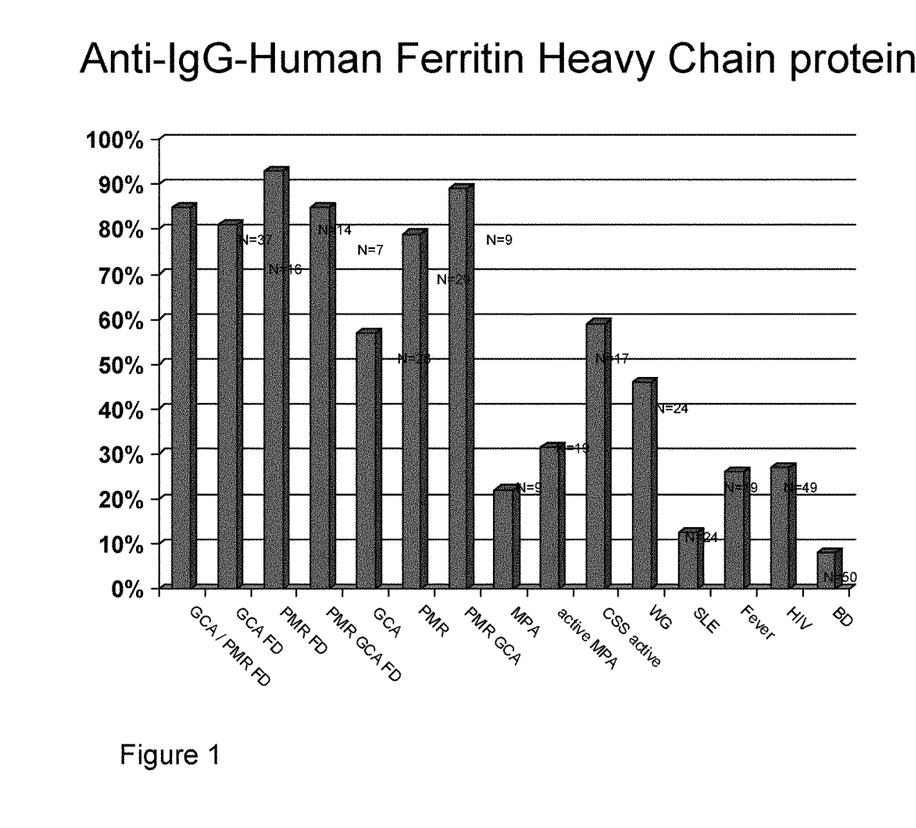
In FIG. 1 the percentage of positive patients for the human IgG anti-ferritin heavy chain antibodies in the following diseases are shown: GCA/PMR FD=giant cell arteritis/polymyalgia rheumatica (first diagnosis), GCA FD=giant cell arteritis (first diagnosis), PMR (FD)=polymyalgia rheumatica (first diagnosis), PMR GCA FD=polymyalgia rheumatica giant cell arteritis (first diagnosis), GCA=giant cell arteritis, PMR=polymyalgia rheumatica, PMR GCA=polymyalgia rheumatica giant cell arteritis, MPA=microscopic polyangiitis, active MPA=active microscopic polyangiitis, CSS active=Churg-Strauss-syndrome (active), WG=Wegener's granulomatosis, SLE=systemic lupus erythematosus, fever, HIV=human immune deficiency virus, and BD=blood donors.
Figure 2:
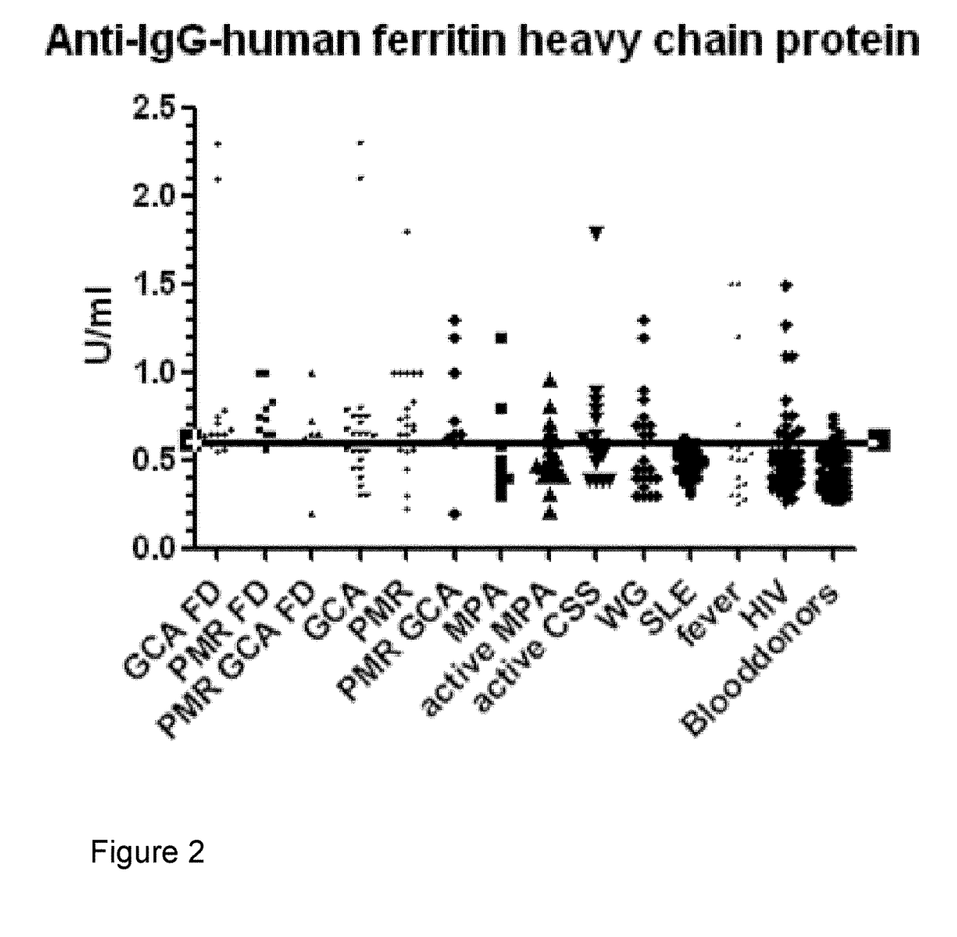
Figure 3:
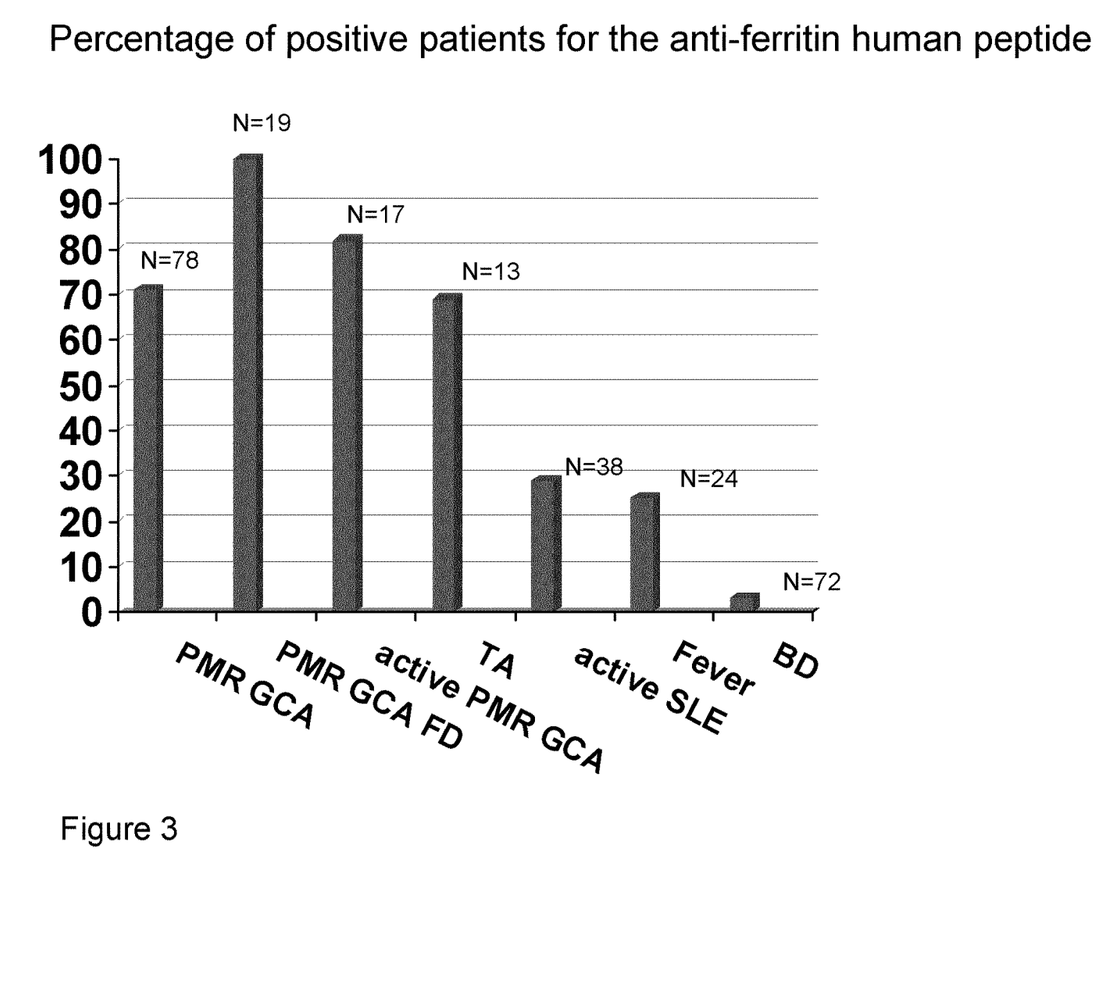
In FIG. 3 the percentage of positive patients for the anti-ferritin human peptide corresponding to the peptide of Seq. ID. No. 3 in the following diseases are shown: PMR GCA=polymyalgia rheumatica giant cell arteritis, PMR GCA FD=polymyalgia rheumatica giant cell arteritis (first diagnosis), PMR GCA active=active polymyalgia rheumatica giant cell arteritis, TA=Takayasu's arteritis, active SLE=active systemic lupus erythematosus, fever, and BD=blood donors.
Figure 4:
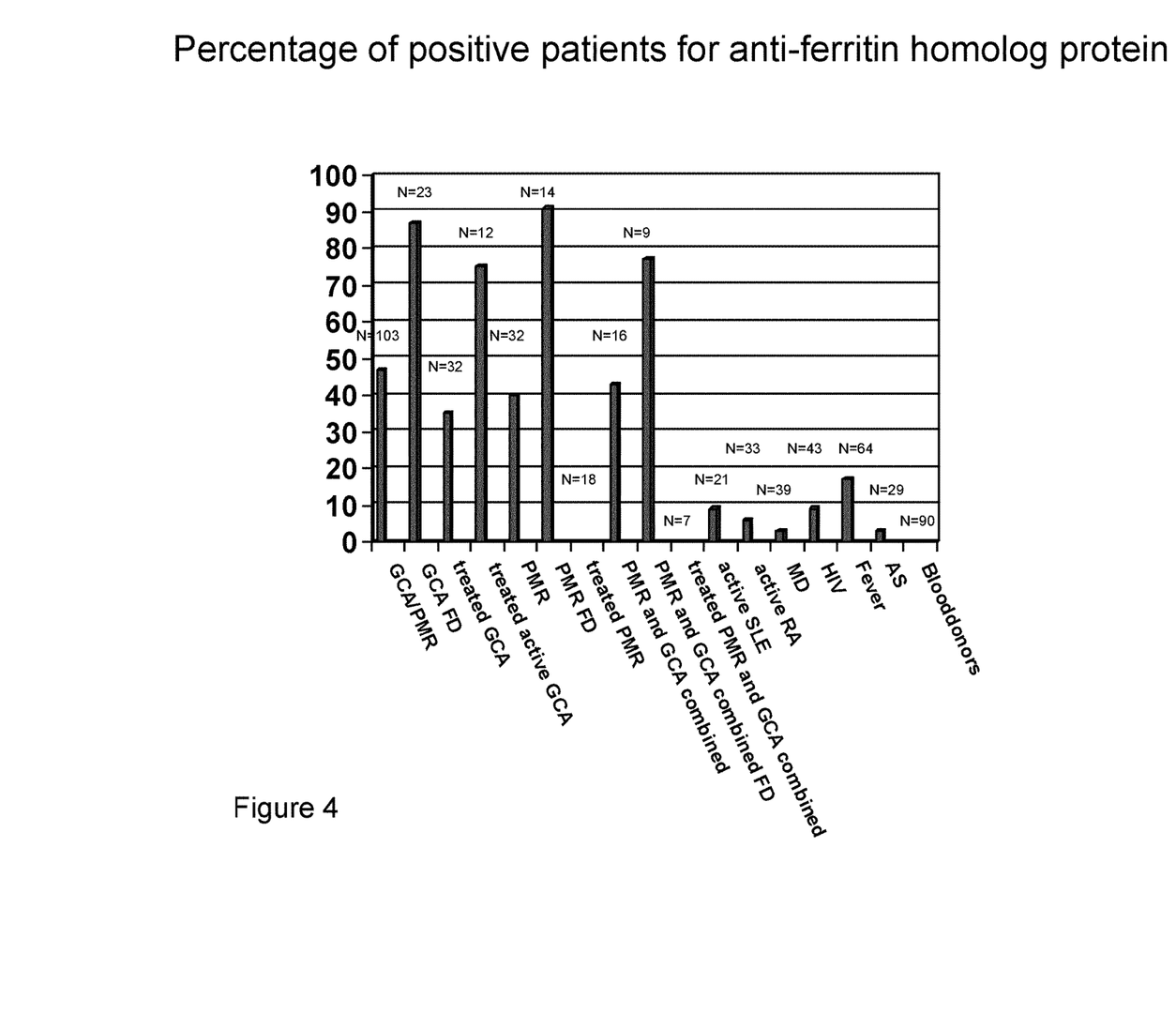

In a first aspect, the present invention relates to a method for diagnosing the presence or the risk of development, or for the therapy control of vasculitis, in particular, of large vessel vasculitis, like giant-cell arteritis (GCA), polymyalgia rheumatica (PMR) and Takayasu's arteritis, in a subject comprising
  a. providing a biological sample from the subject, like obtaining from the subject a biological sample, and
  b. analyzing the sample for the presence of antibodies against ferritin, preferably against ferritin heavy chain, or immunoreactive peptides thereof,
whereby the presence of antibodies against ferritin, preferably against ferritin heavy chain, or immunoreactive peptides thereof, is indicative for the presence or the risk of development, or for the therapy control of vasculitis, preferably of large vessel vasculitis, like GCA, PMR and Takayasu's arteritis.

In an embodiment of the present invention, the methods according to the present invention are in vitro methods.

That is, the present invention is based on the observation of the present inventors that subjects afflicted with vasculitis, in particular, with large vessel vasculitis, like giant-cell arteritis, polymyalgia rheumatica and Takayasu's arteritis, or e.g. microscopic polyangitis (MPA), Churg-Strauss-syndrome (CSS) and/or Wegener's granulomatosis or having risk of developing vasculitis, in particular large vessel vasculitis, like giant-cell arteritis, polymyalgia rheumatica and Takayasu's arteritis, or i.e. microscopic polyangitis (MPA), Churg-Strauss-syndrome (CSS) and/or Wegener's granulomatosis, have antibodies against ferritin, typically against the ferritin heavy chain, or immunoreactive peptides thereof.

Ferritin is an ubiquitous intracellular iron storing and releasing protein found in almost all living organisms (including bacteria, algae, higher plants and animals). It is a globular protein 450 kDa complex consisting of 24 protein subunits. In vertebrates, these subunits are of both, light (L) and heavy (H) type, their sequences being about 50% analogous. In E. coli similarity of 20% to human H-ferritin exists (Andrew, S. C. et al., J Inorganic Biochem, 1992, 47: 3-4, 161).

The term "ferritin" as used herein refers generally to a ferritin peptide. The term "ferritin" includes also fragments of ferritin containing an immunoreactive peptide. The ferritin peptide may be ferritin derived from eukaryotes or prokaryotes. For example, the ferritin may be human ferritin, non-human eukaryotic or prokaryotic ferritin which is an analog of the eukaryotic heavy chain ferritin, like bacterial ferritin, or immunoreactive peptides derived from eukaryotic or prokaryotic ferritin. Immunoreactive peptides are peptides of at least 7 amino acid residues, like 8 to 11 amino acid residues or longer. Immunoreactive peptides of ferritin comprise an epitop of an anti-ferritin antibody, like an autoantibody.

The present invention demonstrates that ferritin, in particular, heavy chain ferritin or immunoreactive peptides thereof, represents an entity to which antibodies can be found in subjects afflicted with vasculitis, in particular, with large vessel vasculitis, like GCA, PMR and Takayasu's arteritis. Hence, determining the presence of antibodies against ferritin (e.g. human ferritin alone, bacterial ferritin alone or a combination of both) is indicative of the presence or the risk of development, or for the therapy control of vasculitis, in particular of large vessel vasculitis, like GCA, PMR and Takayasu's arteritis, or e.g. MPA, CSS and/or Wegener's granulomatosis, in a subject. In particular, antibodies against the heavy chain ferritin and/or the prokaryotic analog thereof, or immune reactive peptides thereof, e.g. against the protein sequence(s) according to Seq. ID No. 1 (of human origin) and/or Seq. ID No. 2 (of bacterial origin) are detected. In a preferred embodiment, the immune reactive peptides include the peptides of Seq ID No. 3, 4, 5 and 6. The immune reactive peptides may be used singly or in combination of at least two of said immune reactive peptides. In a particular preferred embodiment, the method comprises the use of the immune reactive peptides of Seq ID Nos. 3, 5 and 6.

As demonstrated in the examples, the determination of antibodies against at least one of these molecules allows identifying individuals suffering from vasculitis, particularly of large vessel vasculitis, like GCA, PMR and Takayasu's arteritis.

Particular preferred, the immune reactive peptide of ferritin is derived from the N-terminal region of the heavy chain of ferritin, preferably of human heavy chain ferritin, or its analogs in prokaryotes. For example, the ferritin peptide is any one of Seq. ID No. 3 or 4. In another preferred embodiment, a mixture of two or more immune reactive peptides is used, in particular, a combination of Seq ID Nos. 3, 5 and 6.

In particular, it is demonstrated herein that determining the presence of antibodies against ferritin, in particular, against the ferritin heavy chain and/or bacterial ferritin, allows a specific diagnosis of vasculitis, typically of large vessel arteritis, like GCA, PMR and Takayasu's arteritis, in particular, at early stages. Until today, said diseases can be diagnosed by extensive and cost-intensive diagnosis or exclusion of other diseases, disorders or conditions, only. Thus, it is possible for the first time to diagnose the presence or the risk of development of vasculitis, in particular of large vessel vasculitis, like GCA, PMR and Takayasu's arteritis, in a subject with a simple test system or test kit based on the method described herein. Further, it is possible to allow therapy control of subjects afflicted with vasculitis, in particular, large vessel vasculitis, like GCA, PMR and Takayasu's arteritis.

For example, the present invention allows identifying the therapy regimen of an individual in need thereof. That is, identifying the presence of antibodies against ferritin, in particular heavy chain ferritin or immune reactive peptides thereof, suggests a therapy comprising B-cell depletion, inducing tolerance in T-cells or to any other therapy in order to eliminate ferritin specific antibodies. In a preferred embodiment, the presence of antibodies against both, human ferritin and bacterial protein is determined. That is, by determining the presence of antibodies against both, human ferritin, e.g. against ferritin heavy chain, and bacterial ferritin, or immunoreactive peptides thereof, the specificity of diagnosing large vessel vasculitis, like GCA, PMR and Takayasu's arteritis is almost 100%.

The terms "patient" and "subject" are used interchangeably and refer to patients and subjects of humans or other mammals and includes any individual it is desired to examine or treat using the methods of the invention. However, it will be understood that "patient" does not imply that symptoms are present.

The term "biological sample" as used herein refers to a sample that may be extracted, untreated, treated, isolated, and concentrated from a patient. Suitably, the biological sample is selected from any part of the patient's body, including but not limited to hair, skin, nails, tissues or body fluids, such as saliva, synovia and blood. It is preferred that the samples are from the blood of said individual, like from the sera.

Throughout this specification, unless the content requires otherwise, the word "comprise" will be understood to imply the inclusion of a stated step or element or group of steps or elements but not the exclusion of any other step or element or group of steps or elements.

As used herein, the terms "comprising", "comprises" and comprised of" are synonymous with "including", "includes" or "containing", "contains", and are inclusive or open ended and do not exclude additional, non-recited members, elements or method steps. It will be appreciated that the terms "comprising", "comprises", and "comprised of" as well as "including", "includes", or "containing", "contains" as used herein comprise the terms "consisting of", "consists" and "consists of".

All references cited in the present specification are hereby incorporated by reference in their entirety. In particular, the teachings of all references herein specifically referred to are incorporated by reference.

With the term "providing" is meant that the sample provided is an isolated sample originating from the subject.

With the term "obtained from" is meant that a sample such as, for example serum has been isolated from or derived from a particular source of the subject. For example, the extract can be obtained from tissue or a body fluid isolated directly from the subject. For clarification, the term "obtained from" does not include the surgical step itself but relates to an isolated sample.

As used herein the terms "a", "an" and "the" mean "one or more" when used in this application, including the claims. Unless defined otherwise, all technical and scientific terms used herein have the same meaning as commonly understood to one of the ordinary skilled in the art to which the present disclosed subject matters belongs.

The terms "diagnosing" and "diagnosis" as used herein refers to methods by which a skilled artisan can estimate and even determine whether or not a subject is suffering from a given disease, disorder or condition. The skilled artisan makes the diagnosis on the basis of one or more diagnostic indicators, namely antibodies, the amount (including presence or absence) of which is indicator for the presence, severity, or absence of the condition.

Along with diagnosis, therapy control and clinical prognosis is also an area of great concern and interest. It is important to know the severity of the disease as well as the activity of the disease in order to design the most effective therapy.

Hence, "making a diagnosis" or "diagnosing" as used herein may further include making a prognosis which can provide for predicting a clinical outcome, selecting an appropriate treatment, or monitoring current treatment and potentially change the treatment based on the measure of a diagnostic antibody.

The term "determining" or "analyzing" as used herein refers to assessing the presence, absence, quantity, level or amount of the respective antibodies within the subject derived sample, including qualitative or quantitative concentration levels of said substances otherwise evaluating the values or categorisation of a subject clinical parameter.

It has been determined by the inventors that antibody production against ferritin, in particular heavy chain ferritin, or immune reactive peptides thereof, can be correlated with the presence of vasculitis, in particular, large vessel vasculitis, like GCA, PMR and Takayasu's arteritis.

In addition, in some embodiments of the presently disclosed subject matter, multiple determinations of the antibodies over time can be made to facilitate stratification, diagnosis and/or prognosis.

Furthermore, its possible to determine multiple immune reactive peptides derived from the heavy chain ferritin to obtain a sensitive test and method for determining vasculitis and the onset thereof, in particular, of GCA, PMR and Takayasu's arteritis. In particular, using a combination of Seq ID Nos. 3, 5 and 6 is very effective.

In some embodiments of the methods disclosed herein, detecting, determining or analyzing the presence of the antibodies in the sample can include binding the antibodies to antigen and then detecting either the binding event or the presence of the antibody isolated from the biological sample. Exemplary techniques for detecting the antibodies include, but are not limited to, enzyme-linked immunosorbent assay (ELISA), radio immunoassay (RIA), multiplex immunoassay, immunoprecipitation and immunoblotting (including for example western blotting and dot blotting).

The skilled person is well aware of useful immunodetection methods allowing analyzing the sample for the presence or absence of antibodies against ferritin, in particular heavy chain ferritin, or immunoreactive peptides thereof. For example, the biological sample obtained from the subject is contacted with an antigen, namely with ferritin or oligo-, polypeptide or protein containing the antibody immunoreactive peptide including a ferritin epitope, thus, allowing binding of the antibody to said peptide. In this connection, the term "polypeptide" or "protein" which are used interchangeably herein, refer to a polymer of amino acids heaving a length of at least 50 aa. The term "oligopeptide" refers to a polymer of amino acids heaving a length of from 5 to 49 aa. The term "peptide" includes polypeptides, oligopeptides as well as proteins. Particularly useful oligopeptides are the peptides of Seq ID Nos. 3, 5 and 6 which may be used alone or, preferably, in combination.

Contacting the chosen biological sample of the antigen under conditions effective and for a period of time sufficient to allow the formation of immune complexes, is generally a matter of adding the composition to the sample and incubating the mixture for a period of time along enough for the antibodies to form immune complexes with the antigens presented. Said antigen antibody mixture can be detected by known means and methods. That is, detection of immune complex formation of antigen autoantibody can be achieved through the application of numerous approaches. These methods are generally based upon the detection of a label or marker, such as any radioactive, fluorescent, biological or enzymatic tags or labels of standard use in the art. Of course, one may find additional advantages through the use of a secondary binding ligand such as a second antibody or a biotine/avidine (streptavidine) ligand binding arrangement as it is known in the art.

In some embodiments, the primary immune complex can be detected by a second binding ligand that has binding affinity for the antigen or the antibody presented in the sample, for example reactivity to the Fc region of the antibodies or having reactivity to a region of the antigen different to the binding region of the antibody. In these cases, the second binding ligand can be linked to a detectable label or marker molecule. The second binding ligand is itself often an antibody which may thus be termed a secondary antibody. Typically, the primary immune complexes are contacted with the labelled, secondary binding ligand or antibody, under conditions effective and for a period of time sufficient to allow the formation of secondary immune complexes. The secondary immune complexes are then generally washed to remove off any unbound labelled secondary antibodies or ligands, and the remaining label in the secondary immune complex is then detected.

The second binding ligand, such as an antibody, having binding activity for either the antigen or antibody, may also be used to bind to the primary immune complexes. The second binding ligand contains an enzyme capable of processing a substrate detectable to a product and, hence, amplifies a signal over time. After washing, the secondary immune complexes are contacted with substrate, permitting detection. Alternatively, comparative immunodetection may be used. The skilled person is well aware of suitable methods.

It is particularly preferred that the biological sample is a body fluid, preferably blood. In particular, the biological sample is serum of the subject to be diagnosed.

Further, in another embodiment, the methods according to the present invention allows for the stratification of the therapeutic regimen of a subject afflicted with vasculitis, in particular, with large vessel vasculitis, like GCA, PMR and Takayasu's arteritis or being at risk of developing vasculitis, typically large vessel vasculitis, like GCA, PMR and Takayasu's arteritis.

That is, the present invention allows identifying the status of disease, in particular, the active state of the disease in a subject afflicted with vasculitis, typically with large vessel vasculitis, like giant-cell arteritis, polymyalgia rheumatica and Takayasu's arteritis.

The antibodies to be detected may be of the IgA and/or IgG type. That is, it is possible to determine the presence of the IgA and/or IgG antibodies in the biological sample obtained from the subject. Although it is sufficient to detect only one type of antibodies, either IgA or IgG antibodies, it is preferred that both IgA and IgG antibodies against ferritin are detected. In a particular preferred embodiment, the subject is a human and the antibodies are human autoantibodies.

In a further embodiment, the presently disclosed subject matter provides test kits or diagnostic kits for the use in a method according to the present invention. In particular, immunological kits for use in detecting antibodies in biological samples allowing diagnosis of vasculitis, particularly of large vessel vasculitis, like GCA, PMR and Takayasu's arteritis. That is, the present invention provides a test kit for use in a method according to the present invention for diagnosing the presence of the risk of a development as well as for the therapy control of vasculitis, particularly large vessel vasculitis, like GCA, PMR and Takayasu's arteritis, in a subject comprising means or determining antibodies against ferritin, preferably against ferritin heavy chain, or immunoreactive peptides derived from ferritin in a biological sample of a subject to be tested and instructions on how to use the test kit. In preferred embodiment said test kit is an ELISA.

Such kits can generally comprise one or more antigens, namely oligo- or polypeptides of ferritin that can immunoreact with the antibodies. Typically, the immunodetection kits will comprise in suitable container(s), one or more antibody immunoreactive peptide antigens derived from ferritin. Said antigens useful in the presently claimed methods and test kits may be the full ferritin or immunoreactive peptides derived therefrom. For example, the antigens may be a combinative of immunoreactice peptides of Seq ID Nos. 3, 5 and 6.

In certain embodiments, the antigen can be provided bound to a solid support, such as for example a column matrix or a well of a microtiter plate, a membrane, beads, dip sticks or the like. Alternatively, the support can be provided as a separate element of the kit.

That is, the test kit according to the present invention for diagnosing vasculitis, particularly large vessel vasculitis, like GCA, PMR and Takayasu's arteritis, includes beside the antigen a detection agent for the antibodies which may be an antibody, antibody fragment etc. In addition, the kit may comprise more than one detection agent. If required, the kit further comprises substrate and further means for allowing reaction with an enzyme used as label for the detecting agent which may be an antibody.

The immunodetection agents of the kit can include detectable labels that are associated with or linked to the given detecting agent, in particular, the detecting antibody. Detectable labels that are associated with or attached to a secondary binding ligand are also contemplated. Detectable labels include dyes, illuminescent or fluorescent molecules, biotin, radiolabels or enzymes. Typical examples for suitable labels include commonly known fluorescent molecules, like rhodamine, fluorescein, green fluorescent protein or luciferase, or alkaline phosphatase and horseradish peroxidase as examples for suitable enzymes.

Optionally, the kits further comprise positive and negative controls for verifying the results obtained when using the kit. The components of the kits can be packaged either in aqueous medium or lyophilised form and, in addition, the kits comprise one or more containers allowing to conduct the detection. In addition, the test kit comprises instructions for use of the kit.

Moreover, the present invention relates to the use of ferritin heavy chain, immune reactive sequences or analogs thereof in the diagnosis, risk assessment or therapy control of vasculitis, preferably of large vessel vasculitis, like GCA, PMR and Takayasu's arteritis. Typically, the use is in vitro.

Finally, the present invention relates to the use of peptides derived from heavy chain ferritin including immune reactive peptides in prophylaxis and/or treatment of vasculitis, in particular, of large vessel vasculitis, like GCA, PMR and Takayasu's arteritis. That is, the use of heavy chain ferritin peptides including the immune reactive peptides of said molecules allow to induce tolerance, thus, being useful in prophylaxis and therapy of vasculitis, in particular, of large vessel vasculitis, like giant-cell arteritis, polymyalgia rheumatica and Takayasu's arteritis. For example, ferritin, immunoreactive peptides thereof, may be used for systemic or local therapy of diseases, disorders or conditions which are associated with an immunoreaction against said compounds. The administration thereof may be effected orally, parenterally or via mucosal membranes.

Hence, the present invention provides pharmaceutically compositions containing heavy chain ferritin molecules including immunoreactive peptides for use in the prophylaxis and treatment of the disease identified herein as well as in diseases, disorders or conditions associated with an immune reaction against these compounds. The pharmaceutical composition may be provided in a suitable form. The skilled person is well aware of useful forms, dosages etc.

EXAMPLES

The following examples have been included to illustrate modes of the present disclosed subject matter. In light of the present disclosure and the general level of the skilled in the art, those of skilled will appreciate that the following examples are intended to be exemplary only and that numerous changes, modifications and alterations can be employed without departing from the scope of the present disclosed subject matter.

Example 1

Sera of patients with different inflammatory and rheumatic diseases were screened via protein array technology.

New markers of vasculitis have been identified which have been evaluated further for frequency and association by different ELISA.

The evaluation was performed with sera of patients with giant cell arteritis polymyalgia rheumatica, Churg-Strauss-syndrome, Wegener's granulomatosis, microscopic polyangiitis (active and non-active), and with sera of controls (blood donors, patients with systemic lupus erythematosus, malignant diseases, somatic pain syndrome, fever, HIV infected persons and patients with rheumatoid arthritis). The patients had been well characterized with regard to the disease activity, demographic data and treatment. The sera of the patients and of the controls had been stored in a −20° C. freezer until use.

For performing the ELISA tests, 96 well plates (Nunc Maxisorb) were coated with 20 µg recombinant full length human ferritin heavy chain (183 amino acids, purchased from Abcam, Taiwan)(Seq. ID. No. 1), or with 20 µg of a peptide consisting of the N-terminal 27 amino acids of the human ferritin heavy chain (synthesized by Biomatik, U.S.A.) (Seq. ID. No. 3) or with 20 µg of the first (N-terminal) 27 amino acids of ferritin of *Staphylococcus epidermidis* (synthesized by Biomatik, U.S.A.)(Seq. ID. No. 4). The plates were incubated with sera in a 1:100 dilution in PBS for 30 to 60 minutes at room temperature. As a standard, a serum of a patient with highly active vasculitis was used. The concentration of antibodies in this serum was defined as 10 U/ml for IgG-type antibodies against human ferritin heavy chain and the ferritin peptides as well as for IgA-type ferritin antibodies. After 30 to 60 minutes incubation, the plates were washed 3 times with PBS. Next, 100 µl of a secondary peroxidase-goat anti-human IgG or IgA antibody labelled with horse radish peroxidase (HRP) (Jackson ImmunoResearch Europe Ltd.) was added in a dilution of 2:10000 or 2 µl in 8 ml PBS and 2 ml 5% BSA. The plates were incubated for 30 minutes at room temperature and washed 3 times with PBS. The color reaction was performed with tetramethylbenzidine (TMB) (Therma Scientific) for up to 15 minutes according to the manufacturer's instructions and the ODs were read at 450 nm in an ELISA reader.

The test for IgG-type antibodies against human heavy chain ferritin, against the human ferritin peptide and the *Staph. epidermidis*-derived ferritin peptide ("ferritin analog protein") had a sensitivity for untreated giant cell arteritis and/or polymyalgia rheumatica at first diagnosis of 87%, 100% and 87%, respectively, and a specificity (considering only the non-autoimmune controls) of 81%, 92% and 93%, respectively.

In addition, it has been found that a in combination of immunoreactive peptides derived from the ferritin protein is favourable. In particular, a combination of the immunoreactive peptides of Seq ID Nos. 3, 5 and 6 demonstrates a reliable sensitive and specific method for diagnosing giant cell arteritis and polymyalgia rheumatica not only at first diagnosis but also at different disease stages including active stages as well as stages of partial remission etc.

PREFERRED EMBODIMENTS

1. A method for diagnosing the presence or the risk of development, or for the therapy control of vasculitis, preferably of large vessel vasculitis, like giant-cell arteritis (GCA), polymyalgia rheumatica (PMR) and Takayasu's arthritis, in a subject comprising
   a. obtaining from the subject a biological sample, and
   b. analyzing the sample for the presence of antibodies against ferritin or immunoreactive peptides thereof, whereby the presence of antibodies against ferritin or immunoreactive peptides thereof, is indicative for the presence or the risk of development, or for the therapy control of vasculitis, preferably of large vessel vasculitis, like GCA, PMR and Takayasu's arthritis.
2. The method according to embodiment 1, characterized in that the biological sample from the subject, preferably a human subject, is analyzed for the presence of antibodies against human ferritin, preferably against the heavy chain ferritin, and/or bacterial ferritin.
3. The method according to embodiment 1 or 2, characterized in that the biological sample from the subject, preferably a human subject, is analyzed for the presence of antibodies against the protein sequence according to Seq. ID No. 1 and/or Seq. ID No. 2, preferably, for the presence of antibodies against the protein sequence according to Seq. ID No. 3 and/or Seq. ID No. 4.
4. The method according to any one of the preceding embodiments, characterized in that the detected antibodies are of IgA and/or IgG type.
5. The method according to any one of the preceding embodiments, characterized in that the vasculitis is microscopic polyangiitis, Wegener's granulomatosis and/or Churg Strauss syndrome.
6. The method according to any one of the preceding embodiments, characterized in that detection is performed using an immunoassay, preferably with direct or indirect coupling of one reactant to a detectable marker substance.
7. The method according to embodiment 6, characterized in that detection is carried out using an ELISA, RIA, multiplex immunoassay or immunofluorescence assay, western blot, line assay, dot blot assay.
8. The method according to any one of the preceding embodiments wherein the biological sample is selected from blood, tissue or fluid, preferably selected from hair, skin, nails, saliva, synovia, liquor and blood.
9. The method according to embodiment 8 wherein the biological sample is a body fluid, preferably blood, in particular serum.
10. The method according to any one of the preceding embodiments for the stratification of the therapeutic regimen of a subject afflicted with vasculitis, preferably large vessel vasculitis, like GCA, PMR and Takayasu's arteritis, or being at risk of developing vasculitis, preferably large vessel vasculitis, like GCA, PMR and Takayasu's arteritis.
11. The method according to any one of the preceding embodiments for identifying the status of disease, in particular, the activity of the disease in a subject afflicted with vasculitis, preferably large vessel vasculitis, like GCA, PMR and Takayasu's arteritis.
12. A test kit for use in a method according to anyone of embodiments 1 to 11 for diagnosing the presence or the risk of a development as well as for therapy control of vasculitis, preferably large vessel vasculitis, like giant-cell arteritis (GCA), polymyalgia rheumatica (PMR) and Takayasu's arteritis, in a subject comprising means of determining antibodies against ferritin or immunoreactive peptides thereof, preferably human ferritin, more preferably the heavy chain ferritin, and/or bacterial ferritin, in a biological sample of a subject to be tested and instructions on how to use said test kit.
13. The test kit according to embodiment 12 which is an ELISA, RIA, multiplex immunoassay or immunofluorescence assay, western blot assay, line assay or dot blot assay.

14. Use of ferritin or an immunoreactive peptide thereof, preferably human ferritin, more preferably of the heavy chain ferritin, and/or bacterial ferritin, in the diagnosis, risk assessment or therapy control of vasculitis, preferably of large vessel vasculitis, like giant-cell arteritis (GCA), polymyalgia rheumatica (PMR) and Takayasu's arteritis.

15. Pharmaceutical composition containing ferritin, or an immunoreactive peptide thereof, preferably human ferritin, more preferably the heavy chain ferritin, and/or bacterial ferritin, for use in the prophylaxis and/or treatment of vasculitis, preferably of large vessel vasculitis, in particular GCA, PMR and Takayasu's arteritis.

The invention claimed is:

1. A method for the treatment of vasculitis in a subject comprising
   a. analyzing a biological sample obtained from the subject for the presence of antibodies against ferritin or immunoreactive peptides thereof,
   b. determining the subject has or is at risk of developing vasculitis if antibodies against ferritin or immunoreactive peptides thereof are determined to be present in the biological sample, and
   c. treating the subject diagnosed with vasculitis by administering to the subject a therapy that reduces the level of ferritin antibodies in the subject.

2. The method of claim 1, wherein said therapy comprises B cell depletion or the induction of tolerance in T cells.

3. The method according to claim 1, wherein the vasculitis is large vessel vasculitis selected from the group consisting of giant-cell arteritis (GCA), polymyalgia rheumatica (PMR) and Takayasu's arteritis.

4. The method according to claim 1, wherein the biological sample from the subject is analyzed for the presence of antibodies against human ferritin and/or bacterial ferritin.

5. The method according to claim 4, wherein the sample is analyzed for the presence of antibodies against the heavy human chain ferritin.

6. The method according to claim 1, wherein the biological sample from the subject is analyzed for the presence of antibodies against the protein sequence according to Seq. ID No. 1 and/or Seq. ID No. 2.

7. The method according to claim 6, wherein the sample is analyzed for the presence of antibodies against the protein sequence according to Seq. ID No. 3, Seq. ID No. 4, Seq. ID No. 5 or Seq. ID No. 6.

8. The method according to claim 1, wherein the antibodies against ferritin or immunoreactive peptides thereof are of IgA and/or IgG type.

9. The method according to claim 1, wherein the vasculitis is microscopic polyangiitis, Wegener's granulomatosis and/or Churg Strauss syndrome.

10. The method according to claim 1, wherein the analyzing step is performed using an immunoassay.

11. The method according to claim 10, wherein the immunoassay is an ELISA, RIA, multiplex immunoassay or immunofluorescence assay, western blot, line assay, or dot blot assay.

12. The method according to claim 1, wherein the biological sample is a tissue or body fluid, selected from hair, skin, nails, saliva, synovia, liquor, serum and blood.

13. The method according to claim 12, wherein the biological sample is a body fluid selected from saliva, synovia, liquor, serum and blood.

14. The method according to claim 13, wherein the biological sample is serum.

* * * * *